United States Patent [19]
Sugiura et al.

[11] Patent Number: 5,902,458
[45] Date of Patent: *May 11, 1999

[54] METHOD OF SEPARATING SESAMIN ANALOGUES

[75] Inventors: Masato Sugiura; Masanori Inayoshi; Shigeo Sakurai, all of Aichi, Japan

[73] Assignee: Takemoto Yushi Kabushiki Kaisha, Aichi, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/837,546

[22] Filed: Apr. 21, 1997

[30] Foreign Application Priority Data

Apr. 23, 1996 [JP] Japan ..................................... 8-127903
Mar. 19, 1997 [JP] Japan ..................................... 9-085807

[51] Int. Cl.⁶ ....................................................... B01D 3/34
[52] U.S. Cl. .................................. 203/37; 203/93; 203/94; 210/767; 435/134; 549/435
[58] Field of Search ............................ 203/37–38, 91–92, 203/95–98, 93–94, 33, 63; 426/542, 545; 549/435, 464; 252/398; 210/767, 799, 702, 800; 435/134

[56] References Cited

U.S. PATENT DOCUMENTS

| 2,467,903 | 4/1949 | Omohundro et al. | 549/435 |
| 4,283,346 | 8/1981 | Ouchi et al. | 210/671 |
| 4,708,820 | 11/1987 | Namiki et al. | 252/398 |
| 5,209,826 | 5/1993 | Ozaki et al. | 203/38 |

*Primary Examiner*—Virginia Manoharan
*Attorney, Agent, or Firm*—Majestic, Parsons, Siebert & Hsue, P.C.

[57] ABSTRACT

A steam stripping substance, which is obtained by steam distillation of sesame oil under reduced pressure and contains sesamin analogues substantially, is mixed with water, a water-soluble solvent or their mixture serving as solvent. Sesamin analogues are caused to precipitate in this mixed system in the presence of more than one equivalent of an alkali with respect to the acid value of the steam stripping substance. The precipitated sesamin analogues are then separated from the mixed system.

17 Claims, No Drawings

METHOD OF SEPARATING SESAMIN ANALOGUES

BACKGROUND OF THE INVENTION

This invention relates to methods of separating sesamin analogues (inclusive of mixtures of sesamin, its stereo isomers and their enantiomers) which are important substances having many physiologically "active" functions such as enhancement of effects of pyrethrin-type insecticides, acceleration of alcohol metabolism, inhibition of generation of peroxidized lipids in blood and inhibition of cancer. This invention relates to methods of efficiently separating such sesamin analogues at a high purity ratio and at a high yield from a steam stripping substance obtained by steam distillation of sesame oil under a reduced pressure condition.

Conventional methods of separating sesamin analogues from a steam stripping substance obtained by steam distillation of sesame oil under a reduced pressure condition includes (1) the method of subjecting the steam stripping substance to a molecular distillation process as disclosed in Japanese Patent Publication Tokko 7-25764 (U.S. Pat. No. 5,209,826); and (2) the method of mixing the steam stripping substance with ethanol, leaving the mixture quietly for a while and thereafter subjecting the supernatant to an adsorption process with resin of methacrylic acid alkyl ester as disclosed in Japanese Patent Publication Tokko 6-89353. The prior art method (1) described above is disadvantageous firstly in that the molecular distillation itself is a troublesome process, secondly in that the steam stripping substance must undergo a pretreatment process in order that the molecular distillation can be carried out efficiently, and thirdly in that the recovery ratio of sesamin analogues is low from the steam stripping substance. By the prior art method (2) described above, on the other hand, the purity of the sesamin analogues recovered by the adsorption process is low and, if it is desired to improve the purity, a refining process must be included and the recovery ratio of the sesamin analogues from the steam stripping substance turns out to be low as a result.

SUMMARY OF THE INVENTION

It is therefore an object of this invention to overcome the problems of prior art methods that sesamin analogues could not be efficiently separated with high purity and at a high yield.

In view of the object described above, the inventors herein discovered, as a result of their diligent studies, that a preferred method is to prepare a mixed system with the steam stripping substance and a specified solvent and to cause sesamin analogues to be precipitated and separated in the presence of a specified amount of an alkali either directly from this mixed system or by first forming a separate layer of a solvent-soluble fraction.

DETAILED DESCRIPTION OF THE INVENTION

One of the methods according to this invention (hereinafter referred to as Method A) for separating sesamin analogues from a steam stripping substance which contains sesamin analogues substantially and is obtained by steam distillation of sesame oil under a reduced pressure condition is characterized as carrying out the following first and second processes, the first process comprising the step of preparing a mixed system containing the steam stripping substance and its solvent such as water, a water-soluble solvent or a mixed solvent thereof and causing sesamin analogues to be precipitated in the presence of more than one equivalent of alkali with respect to the acid value of this steam stripping substance, and the second process comprising the step of separating the sesamin analogues precipitated in the first process.

Another method according to this invention (hereinafter referred to as Method B) for separating sesamin analogues from a steam stripping substance which contains sesamin analogues substantially and is obtained by steam distillation of sesame oil under a reduced pressure condition is characterized as carrying out the following first and second processes, the first process comprising the steps of mixing the steam stripping substance with an aqueous solution of ethanol serving as its solvent, containing over 40 weight % of ethanol, separating a solvent-soluble fraction from this mixed system and thereafter causing sesamin analogues to be precipitated by adding more than one equivalent of alkali with respect to the acid value of this solvent-soluble fraction, and the second process comprising the step of separating the sesamin analogues precipitated in the first process.

Method A will be described more in detail first. The steam stripping substance obtaining by steam distillation of sesame oil under a reduced pressure condition and at temperature described in aforementioned Japanese Patent Publication Tokko 7-25764 (U.S. Pat. No. 5,209,826) may be used, but it is more advantageous to use a steam stripping substance which is obtained during the deodorization process in the production of sesame oil. These steam stripping substances all contain sesamin analogues substantially but the amount which is contained varies, depending on the apparatus which is used for the steam distillation process, as well as the conditions under which the steam distillation is carried out. Similar variations are also observed with the steam stripping substances obtained during the deodorization process in the production of sesame oil. In a deodorization process using a Girdler-type semi-continuous deodorization apparatus, for example, the content of sesamin analogues in the steam stripping substance remaining at the bottom of the deodorization tower (or the so-called "shell drain") is less than 1 weight %. In the case of a steam stripping substance remaining inside a vacuum booster (or the so-called "booster drain"), it is 5–30 weight %, and it is 3–25 weight % in the case of a steam stripping substance eluted out of a vacuum exhaust system. This invention does not impose any particular limitation as to the steam stripping substances "substantially containing" sesamin analogues but those with concentration greater than one weight %, preferably greater than 3 weight %, and even more preferably greater than 5 weight % can be advantageously utilized. It goes without saying that those with a high content of sesamin analogues should preferably be used in Method A.

The solvent to be used according to Method A is water, a water-soluble solvent or their mixture. Examples of water-soluble solvent include alcohols such as methanol, ethanol and propanol, as well as acetone, tetrahydrofuran, acetonitrile and dimethylformamide. They may be used singly or as a mixture of two or more kinds but it is preferable to use ethanol from the point of view of safety.

When a mixture of water and a water-soluble solvent is used in Method A, the mixing ratio for the water-soluble solvent should preferably be 40 weight % or greater and more preferably be 60 weight % or greater. If the factor of safety is taken into account, it is preferable to use an aqueous solution of ethanol containing ethanol by 40 weight % or more and it is even more preferable to use an aqueous solution of ethanol containing ethanol by 60 weight % or more.

Examples of alkali to be used in Method A include hydroxides of alkali and alkali earth metals, alkali carbonates and alcoholates of alkali metals. They may be used singly or as a mixture of two or more kinds, but sodium hydroxide, potassium hydroxide, sodium carbonate, potassium carbonate, sodium ethylate and potassium ethylate are preferable and potassium hydroxide and potassium carbonate are particularly preferable.

According to Method A, sesamin analogues are precipitated within a mixed system of the steam stripping substance and a solvent in the presence of a specified amount of alkali. The method of causing the alkali to be present in the mixed system does not limit the invention. This may be carried out, for example, (1) by mixing the steam stripping substance with the solvent and thereafter adding an alkali to this mixture, (2) by preliminarily adding an alkali to the solvent and then mixing this with the steam stripping substance, (3) by preliminarily adding an alkali to the steam stripping substance and then mixing this with the solvent, or (4) by adding an alkali at the same time as the steam stripping substance and the solvent are mixed together. Of these, the method of first mixing the steam stripping substance and the solvent and then adding an alkali to this mixed system is preferable.

In any of these methods described above, it is preferable that the amount of alkali to be added to the mixture be over 1 equivalent with respect to the acid value of the steam stripping substance, and it is more preferable that it be no more than ten equivalents, or even more preferably 2-10 equivalents. If more than 10 equivalents of alkali are caused to be present, no corresponding effects can be obtained. In the above, "the amount of alkali" means the amount of the alkali which is finally found in the mixture.

The alkali may be added in the form of a simple substance of the aforementioned alkali products but it is preferable to add them in the form of an aqueous solution. When an aqueous alkali solution is added, its water also serves eventually as a solvent to the steam stripping substance. Thus, when a water-soluble solvent or a mixed solvent is used as the solvent in Method A such that sesamin analogues are precipitated by adding an alkali to the mixed system of the steam stripping substance and such solvent, it is preferable that over 40 weight % of the solvent be eventually a water-soluble solvent, and ethanol in particular.

The invention does not limit the ratio of mixture between the steam stripping substance and the solvent in Method A, but it is normally 100–2000 weight parts of the solvent against 100 weight parts of the steam stripping substance and, more preferably, 200–500 weight parts of the solvent.

Finally, the sesamin analogues thus precipitated are separated in Method A. The invention is not limited by the method of separation. Known methods of separation such as decantation, filtration and centrifugation may be used.

Method B will be described next in detail. The steam stripping substances to be used in Method B are the same as those used in Method A.

The solvent to be used in Method B is an aqueous ethanol solution containing ethanol by 40 weight % or more, and preferably by 70–90 weight %. The alkali products to be used in Method B are the same as those used in Method A.

In Method B, the mixed system of the steam stripping substance and the solvent is left quietly such that the solvent-soluble fraction and the fraction which is not soluble to the solvent are separated into two layers. Since sesamin analogues come to be contained in the solvent-soluble fraction, this fraction is separated from the mixed system and an alkali is added to it for precipitating the sesamin analogues. Both the recovery ratio and the purity of sesamin analogues can thus be improved. In this method, it is preferable to reflux the mixed system before the solvent-soluble fraction is separated in a layer because the recovery ratio and the purity of the sesamin analogues can be further improved.

The amount of the alkali to be added to the solvent-soluble fraction should be more than 1 equivalent with respect to the acid value of the solvent-soluble fraction and more preferably about 2–10 equivalents. If more than 10 equivalents of alkali is added, no corresponding effect is obtained.

The alkali may be added in the form of a simple substance used in Method A described above but it is preferable to be added in the form of an aqueous solution. When an aqueous alkali solution is added, its water also serves eventually as a solvent to the steam stripping substance. Thus, when an aqueous alkali is added to the solvent-soluble fraction separated from a mixed system to cause sesamin analogues to precipitate, it is preferable that the solvent has over 40 weigh % of ethanol.

The ratio of mixture between the steam stripping substance and the solvent in Method B is the same as that for Method A.

Finally, the sesamin analogues thus precipitated from the solvent-soluble fraction are separated from the mixed system. The method of separation is the same as for Method A.

Method A may be carried out, for example, in any of the following six processes:

(1) A mixed system is prepared by adding 400 weight parts of an 80 weight 6 aqueous solution of ethanol as solvent to 100 weight parts of booster drain (sesamin analog content 8.6 weight %, acid value 31, hereinafter referred to as steam stripping substance A) obtained in the deodorization step in the production of sesame oil. To this mixed system is added a 48 weight % aqueous solution of potassium hydroxide (25.8 weight parts, or 4 equivalents as KOH), and the mixture is maintained at 10° C. to cause sesamin analogues to precipitate, and the precipitated sesamin analogues are separated by suction filtration.

(2) A mixed system is prepared by adding 400 weight parts of an 80 weight % aqueous solution of ethanol as solvent to 100 weight parts of steam stripping substance A. To this mixed system is added a 48 weight % aqueous solution of potassium hydroxide (9.7 weight parts, or 1.5 equivalents as KOH), and sesamin analogues are precipitated by holding this mixture at 10° C. The precipitated sesamin analogues are separated by suction filtration.

(3) A mixed system is prepared by adding 1000 weight parts of water as solvent to 100 weight parts of steam stripping substance A. To this mixed system is added a 40 weight % aqueous solution of sodium hydroxide (22.1 weight parts, or 4 equivalents as NaOH), and sesamin analogues are precipitated by holding this mixture at 10° C. The precipitated sesamin analogues are separated by suction filtration.

(4) A mixed system is prepared by adding 250 weight parts of ethanol as solvent to 100 weight parts of steam stripping substance A. To this mixed system is added a 48 weight % aqueous solution of potassium hydroxide (25,8 weight parts, or 4 equivalents as KOH), and sesamin analogues are precipitated by holding this mixture at 10° C. The precipitated sesamin analogues are separated by suction filtration.

(5) A mixed system is prepared by adding 400 weight parts of a 60 weight % aqueous solution of ethanol as solvent to 100 weight parts of steam stripping substance A. To this mixed system is added a 48 weight % aqueous solution of potassium hydroxide (38.7 weight parts, or 6 equivalents as KOH), and sesamin analogues are precipitated by holding this mixture at 10° C. The precipitated sesamin analogues are separated by suction filtration.

(6) Potassium hydroxide (12.4 weight parts) is preliminarily dissolved in 400 weight parts of an 80 weight % aqueous solution of ethanol as solvent, and a mixed system (4 equivalents as KOH) is prepared by adding 100 weight parts of steam stripping substance A to this solution. Sesamin analogues are precipitated by holding this mixture at 10° C. The precipitated sesamin analogues are separated by centrifugation.

Method B may be carried out, for example, in any of the following three processes:

(7) An 80 weight % aqueous solution of ethanol (400 weight parts) as solvent is added to 100 weight parts of stream stripping substance A. It is refluxed for one hour with stirring and then cooled to the room temperature to prepare a mixed system separated into two layers. After the solvent-soluble fraction is separated from this mixed system, a 48 weight % aqueous solution of potassium hydroxide (24.7 weight parts, or 4 equivalents as KOH) is added and mixed with 418 weight parts of this separated solvent-soluble fraction. sesamin analogues are precipitated by holding this mixture at 10° C., and the precipitated sesamin analogues are separated by suction filtration.

(8) A 48 weight % aqueous solution of potassium hydroxide (37.1 weight parts, or 6 equivalents as KOH) is added to 418 weight parts of the solvent-soluble fraction obtained in (7). Sesamin analogues are precipitated by holding this mixture at 10° C. The precipitated sesamin analogues are separated by suction filtration.

(9) A 60 weight % aqueous solution of ethanol (400 weight parts) as solvent is added to 100 weight parts of stream stripping substance A, and it is refluxed for one hour with stirring and then cooled to the room temperature to obtain a mixed system separated into two layers. After the solvent-soluble fraction is separated from this mixed system, a 48 weight % aqueous solution of potassium hydroxide (24.7 weight parts, or 4 equivalents as KOH) is added and mixed with 395 weight parts of this separated solvent-soluble fraction. Sesamin analogues are precipitated by holding this mixture at 10° C., and the precipitated sesamin analogues are separated by suction filtration.

EXAMPLES

Methods A and B will be described more in detail next by way of test examples and comparison examples, but these test examples are not intended to limit the scope of the invention. In what follows, "parts" shall mean weight parts and "%" shall mean weight %.

Test Example 1

An 80% aqueous solution of ethanol (400 parts) as solvent was added to 100 parts of booster drain (sesamin content 8.6% and acid value 31) as steam stripping substance obtained in the deodorization process for the refining of sesame oil to prepare a mixed system. A 48% aqueous solution of potassium hydroxide (25.8 part, or 4 equivalents as KOH) was added to this mixed system, and it was left overnight at 10° C. Sesamin analogues were precipitated and separated from the mixed system by suction filtration. After they were washed with 100 parts of water, they were dried for three hours at 80° C. to obtain 7.2 parts of light yellow powder containing sesamin analogues by 93%. The recovery ratio of sesamin analogues was 78%.

Test Examples 2–5 and Comparison Examples 1 and 2

The same booster drain as in Test Example 1 was used but the kind and amount of the solvent for preparing a mixed system as well as the kind and amount of alkali were varied as shown in Table 1. In other aspects, the conditions were the same as in Test Example 1.

Test Example 6

Potassium hydroxide (12.4 parts) was preliminarily dissolved in 400 parts of an 80% aqueous solution of ethanol as solvent. The same booster drain (100 parts) as used in Test Example 1 was added to this solution and mixed to obtain a mixed system. This mixed system was left overnight at 10° C. to precipitate sesamin analogues. The precipitated sesamin analogues were separated by centrifugation and, after they were washed with 100 parts of water, they were dried for three hours at 80° C. to obtain 6.9 parts of light brown powder containing sesamin analogues by 90%. The recovery ratio of sesamin analogues was 72%. Conditions and results of separation with Test Examples 1–6 and Comparison Examples 1 and 2 are shown also in Table 1. Test Examples 1–6 described above are examples of Method A.

Test Example 7

An 80% aqueous solution of ethanol (400 parts) was added as solvent to 100 parts of the same booster drain as used in Test Example 1. After it was refluxed with stirring for one hour, it was cooled to 20° C. and left overnight at the same temperature to prepare a mixed system. The mixed system thus obtained was already separated into two layers, that is, a layer of a solvent-soluble fraction and another layer of a fraction not soluble to the solvent. After the solvent-soluble layer was separated from this mixed system, a 48% aqueous solution of potassium hydroxide (24.7 parts, or 4 equivalents with respect to the acid value of the solvent-soluble fraction) was added to 418 parts of the separated solvent-soluble fraction (acid value 7.1), and it was left overnight at 10° C. to cause sesamin analogues to precipitate. The precipitated sesamin analogues were separated by suction filtration, washed with 100 parts of water and dried for three hours at 80° C. to obtain 7.2 g of brownish solid containing sesamin analogues by 99%. The recovery ratio of sesamin analogues was 83%.

Test Examples 8 and 9

The same booster drain as in Test Example 1 was used but the kind and amount of the solvent for preparing a mixed system as well as the kind and amount of alkali were varied as shown in Table 2. In other aspects, the conditions were the same as in Test Example 7. Conditions and results of separation with Test Examples 7–9 are shown also in Table 2. Test Examples 7–9 described above are examples of Method B.

It should be clear from the descriptions above that the present invention makes it possible to obtain sesamin analogues efficiently with high recovery ratio and high purity from steam stripping fractions substantially containing sesamin analogues obtainable by steam distillation of sesame oil under a reduced pressure condition.

TABLE 1

| Examples | Steam Stripping Substance (Part) | Solvent (Kind/ Amount) | Alkali (Kind/ Amount/ Equiv.) | Solvent Composition Of mixed system In presence of Alkali (Ethanol/water) | Recovery Ratio of Sesamin Analogues (%) | Purity (%) |
|---|---|---|---|---|---|---|
| Test Examples |
| 1 | 100 | A-1/400 | B-1/25.8/4 | 77.4/22.6 | 78 | 93 |
| 2 | 100 | A-1/400 | B-1/9.7/1.5 | 79.0/21.0 | 65 | 85 |
| 3 | 100 | Water/1000 | B-2/22.1/4 | 0/100 | 62 | 81 |
| 4 | 100 | A-2/250 | B-1/25.8/4 | 95.0/5.0 | 64 | 94 |
| 5 | 100 | A-3/400 | B-1/38.7/6 | 57.1/42.9 | 74 | 91 |
| 6 | 100 | A-1/400 | B-3/12.4/4 | 80/20 | 72 | 90 |
| Comparison Examples |
| 1 | 100 | A-1/400 | B-1/3.2/0.5 | 79.8/20.2 | 10 | 25 |
| 2 | 100 | A-1/400 | B-1/1.6/0.25 | 79.9/20.1 | 0 | — |

In Table 1:

A-1: 80% aqueous solution of ethanol;

A-2: Ethanol;

A-3: 60% aqueous solution of ethanol;

B-1: 48% aqueous solution of KOH;

B-2: 40% aqueous solution of NaOH;

B-3: KOH

Amounts of solvent and alkali which were used are also expressed in weight parts.

TABLE 2

| Example | Steam Stripping Substance (Part) | Solvent (Kind/ Amount) | Soluble Fraction (Amount Acid value) | Alkali (Kind/ Amount/ Equiv.) | Recovery Ratio of Sesamine Analogues (%) | Purity (%) |
|---|---|---|---|---|---|---|
| Test Examples |
| 7 | 100 | A-1/400 | 418/7.1 | B-1/24.7/4 | 83 | 99 |
| 8 | 100 | A-1/400 | 418/7.1 | B-1/37.1/6 | 84 | 98 |
| 9 | 100 | A-3/400 | 395/7.5 | B-1/24.7/4 | 81 | 98 |

In Table 2:

A-1: 80% aqueous solution of ethanol;

A-3: 60% aqueous solution of ethanol;

B-1: 48% aqueous solution of KOH;

Amounts of solvent, soluble fraction and alkali which were used are also expressed in weight parts.

What is claimed is:

1. In a method of separating sesamin analogues from a steam stripping substance which is obtained by steam distillation of sesame oil under reduced pressure and contains substantially sesamin analogues, the improvement wherein said method comprises;

a first step of causing sesamin analogues to precipitate in a mixed system of said steam stripping substance and a solvent in the presence of more than one equivalent and no more than ten equivalents of an alkali with respect to the acid value of said steam stripping substance, said solvent being one or more selected from the group consisting of water, water-soluble solvents and mixtures thereof; and a second step of separating said precipitated sesamin analogues obtained in said first step.

2. The method of claim 1 wherein said first step includes the steps of mixing said steam stripping substance and said solvent to prepare said mixed system and thereafter adding said alkali to said mixed system.

3. The method of claim 2 wherein said alkali is selected from the group consisting of potassium hydroxide, potassium carbonate and mixtures of potassium hydroxide and potassium carbonate.

4. The method of claim 3 further comprising the step of obtaining said steam stripping substance in a deodorization process in a production process of sesame oil.

5. The method of claim 2 further comprising the step of obtaining said steam stripping substance in a deodorization process in a production process of sesame oil.

6. The method of claim 1 wherein said solvent is an aqueous solution of ethanol containing more than 40 weight % of ethanol.

7. In the method of separating sesamin analogues from a steam stripping substance which is obtained by steam distillation of sesame oil under reduced pressure and contains substantially sesamin analogues, the improvement wherein said method comprises:

a first step of causing sesamin analogues to precipitate by mixing said steam stripping substance with an aqueous solution of ethanol containing more than 40 weight % of ethanol serving as a solvent to form a mixed system, separating from said mixed system a solvent-soluble fraction which is soluble to said solvent, and thereafter adding to said solvent-soluble fraction more than one equivalent and no more than ten equivalents of an alkali with respect to the acid value of said solvent-soluble fraction; and a second step of separating said precipitated sesamin analogues obtained in said first step.

8. The method of claim 7 wherein said first step includes the step of refluxing said mixed system before said solvent-soluble fraction is separated.

9. The method of claim 8 wherein said alkali is selected from the group consisting of potassium hydroxide, potassium carbonate and mixtures of potassium hydroxide and potassium carbonate.

10. The method of claim 9 further comprising the step of obtaining said steam stripping substance in a deodorization process in a production process of sesame oil.

11. The method of claim 8 further comprising the step of obtaining said steam stripping substance in a deodorization process in a production process of sesame oil.

12. The method of claim 7 wherein said alkali is selected from the group consisting of potassium hydroxide, potassium carbonate and mixtures of potassium hydroxide and potassium carbonate.

13. The method of claim 12 further comprising the step of obtaining said steam stripping substance in a deodorization process in a production process of sesame oil.

14. The method of claim 7 further comprising the step of obtaining said steam stripping substance in a deodorization process in a production process of sesame oil.

15. The method of claim 1 wherein said alkali is selected from the group consisting of potassium hydroxide, potassium carbonate and mixtures of potassium hydroxide and potassium carbonate.

16. The method of claim 15 further comprising the step of obtaining said steam stripping substance in a deodorization process in a production process of sesame oil.

17. The method of claim 1 further comprising the step of obtaining said steam stripping substance in a deodorization process in a production process of sesame oil.

* * * * *